(12) United States Patent
Fiechter et al.

(10) Patent No.: US 9,216,016 B2
(45) Date of Patent: Dec. 22, 2015

(54) SURGICAL DEVICE FOR MINIMALLY INVASIVE SPINAL FUSION AND SURGICAL SYSTEM COMPRISING THE SAME

(71) Applicant: MEDACTA INTERNATIONAL SA, Castel, San Pietro (CH)

(72) Inventors: Meinrad Fiechter, Lugano (CH); Alfonso Fantigrossi, Turate (IT); Francesco Siccardi, Vico Morcote (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 285 days.

(21) Appl. No.: 14/018,600

(22) Filed: Sep. 5, 2013

(65) Prior Publication Data

US 2014/0066718 A1 Mar. 6, 2014

(30) Foreign Application Priority Data

Sep. 6, 2012 (EP) .................................. 12183377

(51) Int. Cl.
*A61B 1/32* (2006.01)
*A61B 17/02* (2006.01)
*A61B 17/70* (2006.01)
*A61B 17/00* (2006.01)

(52) U.S. Cl.
CPC ......... *A61B 17/0218* (2013.01); *A61B 17/0206* (2013.01); *A61B 17/7077* (2013.01); *A61B 2017/00407* (2013.01); *A61B 2017/00477* (2013.01); *A61B 2017/0256* (2013.01)

(58) Field of Classification Search
CPC combination set(s) only.
See application file for complete search history.

(56) References Cited

U.S. PATENT DOCUMENTS

2006/0247645 A1    11/2006  Wilcox et al.
2012/0303034 A1*  11/2012  Woolley et al. ................. 606/90

OTHER PUBLICATIONS

International Search Report dated Jan. 31, 2013.

* cited by examiner

*Primary Examiner* — Sameh Boles
(74) *Attorney, Agent, or Firm* — Lucas & Mercanti LLP.

(57) ABSTRACT

A surgical device is disclosed which may advantageously perform the functions of both a retractor and a distractor. The device has two retractor blades facing each other and held in a common frame, the retractor blades are insertable into a surgical incision in a patient and moveable away from each other along a main axis (x) so as to widen the surgical incision; and a connecting pin attached at a distal end of each retractor blade. Each connecting pin is attachable to a pedicle screw anchored to respective vertebrae of the patient, so that moving away the two retractor blades along the main axis (x) determines a distraction of the vertebrae.

11 Claims, 5 Drawing Sheets

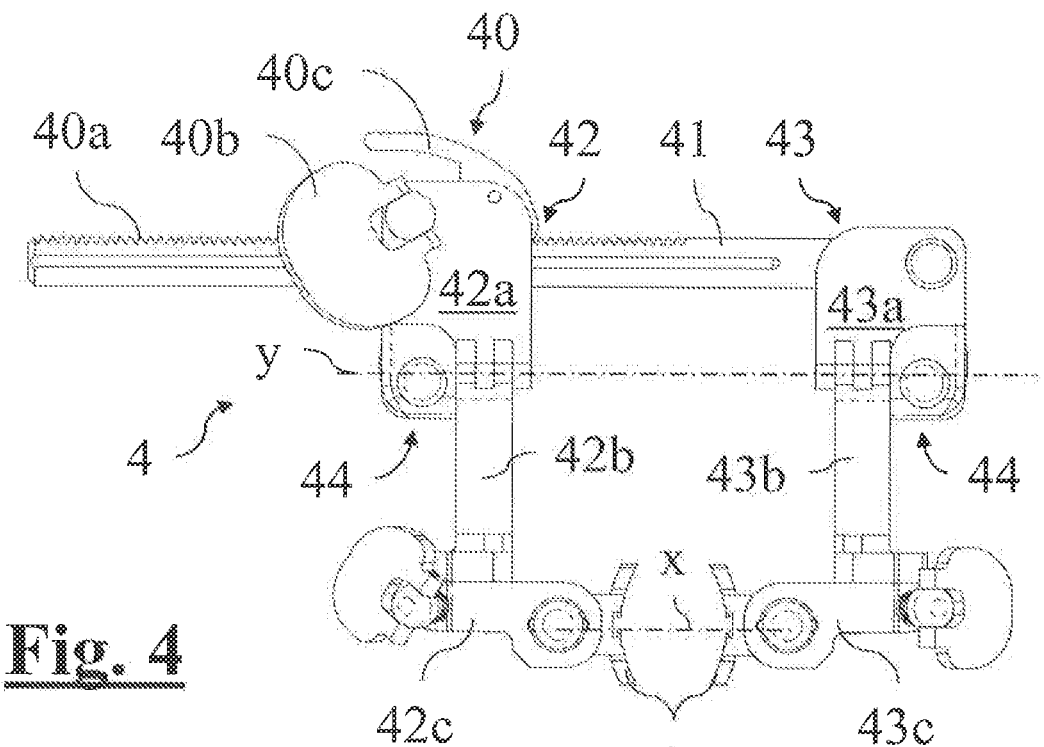
Fig. 4
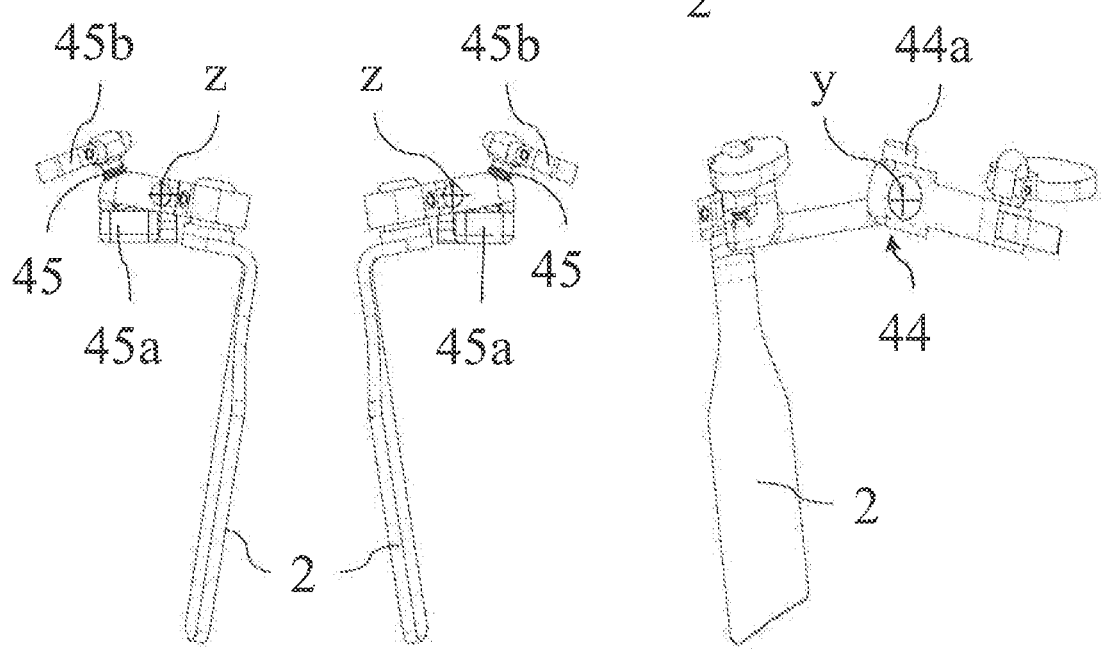
Fig. 5                    Fig. 6

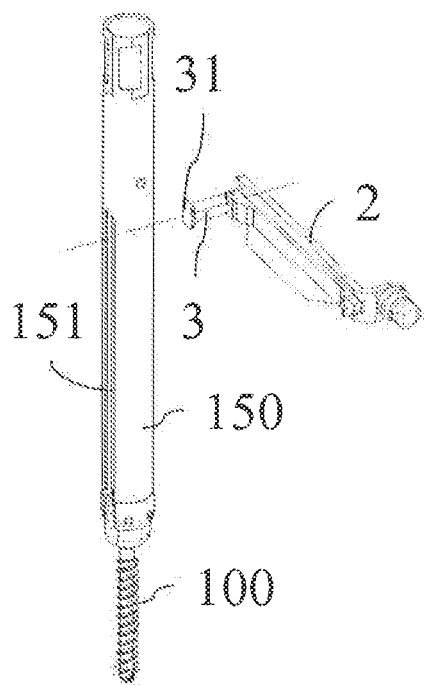
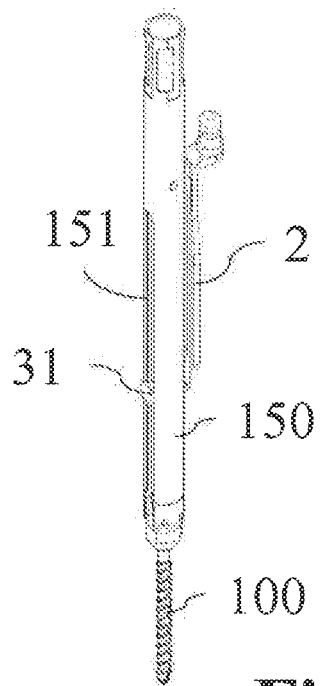
Fig. 13    Fig. 14
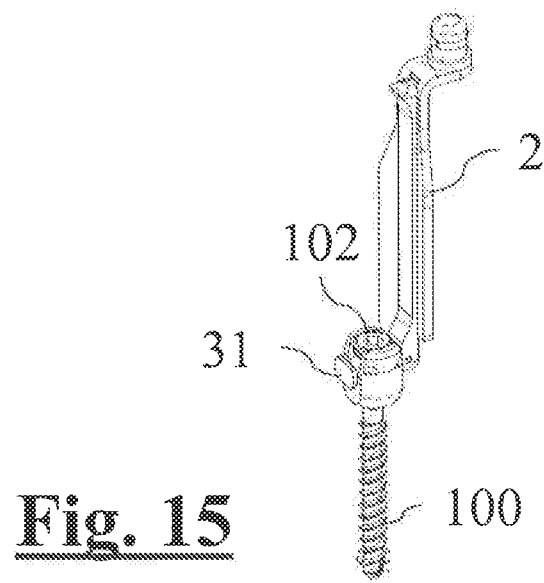
Fig. 15

SURGICAL DEVICE FOR MINIMALLY INVASIVE SPINAL FUSION AND SURGICAL SYSTEM COMPRISING THE SAME

CROSS REFERENCE TO RELATED APPLICATION

This application claims the benefit of European Patent Application No. 12 183377.6 filed Sep. 6, 2012, the contents of which are incorporated herein by reference.

FIELD OF THE INVENTION

The present invention relates to the broad technical field of orthopedic surgery. More specifically, the invention relates to a surgical device to be employed in minimally invasive spinal surgery. The invention further relates to a surgical system comprising the above-mentioned surgical device.

BACKGROUND OF THE INVENTION

Surgical techniques for the treatment of spinal injuries or deformities are usually aimed at joining together two or more vertebrae of the spine, through a process named spinal fusion.

Spinal fusion typically involves the removal of damaged disc material between the two adjacent vertebrae and the subsequent insertion of one or more interbody devices into the emptied disc space, either using an anterior or a posterior approach.

In order to ensure primary stability, the surgeon usually adopts a fixation system that is anchored to the spine by means of orthopedic screws implanted into the pedicles of the vertebrae that are to be fused together. The single screws are connected together by means of rigid or semi-rigid rods, which are conveniently housed within a transversal hole provided in the screw head.

Only recently has the trend toward minimally invasive surgical techniques become also pervasive in the field of spinal surgery, with applications to the above-described spinal fusion procedures.

However, different challenges come with the introduction of these new techniques.

Firstly, it is critical that a sufficient access and visibility of the interbody area are ensured, in particular during operations of discectomy and disc replacement. In order to do so, dedicated retractors have been developed that may be inserted into and appropriately widen the surgical incision.

Secondly, it is often necessary to distract the adjacent vertebrae to be able to operate in the interbody area, either to remove the damaged disc or to insert the replacement body. This task is performed by a surgical distractor device.

The adoption of both a distractor and a retractor may prove difficult to coordinate for the surgeon, adding an unwanted additional complication to a challenging operation.

Systems combining both the functions of a distractor and a retractor have been developed, but these have tended to be excessively bulky and hard to handle due to their plurality of interdependent elements. Moreover, the different operative members inserted in the surgical site may obstruct the visibility and access to the surgical site.

In view of the foregoing, the technical problem underlying the present invention is to provide a surgical device that may perform the functions of both a retractor and a distractor, while at the same time having a simple structure and only a limited number of operative members that are inserted within the surgical site.

SUMMARY OF THE INVENTION

The above-mentioned technical problem is solved by a surgical device comprising: two retractor blades facing each other and held together by a common frame, said retractor blades being insertable into a surgical incision in a patient and moveable away from each other along a main axis so as to widen said surgical incision; the surgical device further comprising a connecting pin attached at a distal end of each retractor blade, each connecting pin being attachable to a pedicle screw anchored to a respective vertebra of the patient, so that moving away the two retractor blades along said main axis determines a distraction of the vertebrae.

A compression of the vertebrae is also possible by moving the two retractor blades toward each other.

A person skilled in the art will readily acknowledge that the invented device may act both as a retractor and as a distractor, depending on the connection with the pedicle screw.

Indeed, it should be noted that pedicle screws typically comprise a bulging head with a U-shaped passage meant to house a connecting rod. Before the insertion of the connecting rod, which may be the last step of the surgical procedure, the U-shaped passage may advantageously house the connecting pin of the surgical device described above. The blades of the device are obviously allowed to diverge in order to exert their retracting function; when attached to two pedicle screws anchored on adjacent vertebrae, the same motion determines a distraction of the bones.

The retractor blades of the device are said to face each other. This wording implies that the blades are substantially set one in front of the other in at least one operative configuration of the device. The wording does not imply parallelism of the blades in the operative configuration. Moreover, the wording does not exclude that the device may have different configurations in which the blades do not face each other.

The retractor blades of the device are preferably curved, having a convex and a concave side. The concave sides of the blade face each other, i.e. they are the inner sides of the blades. The concave outer sides are designed to push on the soft tissue of the patient during retraction.

The connecting pin attached to each retractor blade is preferably directed toward the opposite retractor blade, i.e. attached on an inner side of the retractor blade.

In such a way, the connecting pins face each other and may effectively exert a pulling action on the two pedicle screw to distract the vertebrae.

The connecting pins are preferably orientable so as to be substantially aligned along the main axis when attached to the pedicle screws for distraction.

In such a way, the pins may be perfectly aligned to the line of traction, i.e. the main axis, when performing the distraction.

Each connecting pin may be hingedly connected to the respective retractor blade. In particular, the connecting pin may be hinged about an axis orthogonal to the main axis, so that it can rotate on the mid-plane traversing the two opposite retractor blades.

The rotation angle of the hinge may be limited to ±50° from an orthogonal position of the connecting pin with respect to the retractor blade. In other word, the connecting pin will be orthogonal to the longitudinal axis of the retractor blade in a neutral position. If the retractor blade is in a tilted position instead of being perfectly parallel to the other blade, the connecting pin may be angled up to 50° from the neutral position in order to align with the opposite pin along the main axis.

The hinge advantageously makes the connection of the connecting pin with the U-shaped passage of the pedicle screw easier, especially in case the retractor blade is in an inclined position or in case of irregular bone anatomy.

Each connecting pin may feature a retaining flange at its free end.

Thanks to this retaining flange, the traction force may be exerted on the pedicle screw via the pin, with the flange abutting against the shoulder defined by the arm head at the end of the U-shaped passage.

Each connecting pin of the surgical device may advantageously be releasably attached to the respective retractor blade.

In such a way, when the device is employed as a retractor, the connecting pins may be advantageously removed so that they do not hinder the operation.

A skilled person will understand that the connecting pins may be attached to the blades in a variety of ways. For instance, each connecting pin may be mounted on a sliding connector that is slidingly attachable to an inner side of the respective retractor blade.

In particular, the sliding connector may have an elongated shape, being insertable within a longitudinal groove extending from a proximal end to the distal end of the respective retractor blade.

This solution is particularly advantageous as it allows insertion of the sliding connector from the proximal side, so that the connecting pins may be inserted or removed even when the blades of the surgical device are inserted into the surgical incision.

Moreover, the continuous longitudinal groove allows a free selection of the height of the connecting pin, in order to match the position of the pedicle screw in situ.

The sliding connector may have T-shaped or dove-shaped teeth sliding within the longitudinal groove.

The retractor blades may also be releasably attached to the common frame.

Such a layout allows independent insertion of the retractor blades into the surgical incision, for instance by sliding them over a dilator tube or a percutaneous tube, and a subsequent fixation to the common frame.

The surgical device according to the present invention may further comprise a linear actuator, preferably integrated in the common frame, for relatively moving the retractor blades away from each other along said main axis.

Therefore, a single linear actuator may advantageously operate the device both when performing retraction and distraction.

The common frame may comprise a main bar parallel to said main axis and two arms coupled to said main bar and respectively holding the two retractor blades, said linear actuator moving at least one of said arms along the main bar.

The linear actuator may be for instance a manually operated linear ratchet, so that a return motion of the arm carrying the moveable blade is prevented during retraction and distraction.

The arms may be articulated arms having at least a first hinging axis parallel to the main axis.

The degree of freedom allows a more comfortable positioning of the common frame on the body of the patient.

The adjustment about said first hinging axis may be provided by an angular ratchet.

The angular ratchet prevents unwanted rotation that would move the blades away from the surgical site.

The arms may be articulated arms having at least a second hinging axis orthogonal to the main axis.

Thanks to this degree of freedom, the blades may be inclined, widening the surgical site while the size of the surgical incision remains unvaried.

The adjustment about said second hinging axis may be provided by an adjustment screw. A tip of the screw may be freely rotatable within a fixed portion of the arm while the shank of the screw is threadingly engaged in a through-hole of a hinged portion of the arm.

The above-mentioned technical problem is also solved by a surgical system comprising the surgical device and at least a percutaneous tower, said connecting pins being slidably engageable in longitudinal side openings of said percutaneous tower.

Further features and advantages of the surgical device and of the corresponding system according to the invention shall be made clearer by the description, given herein below, of a specific embodiment described by way of non-limiting example with reference to the accompanying drawings.

BRIEF DESCRIPTION OF THE DRAWINGS

FIG. 4 shows a top view of the surgical device in FIG. 3;

FIG. 5 shows a front view of the surgical device in FIG. 3;

FIG. 6 shows a side view of the surgical device in FIG. 3;

FIG. 13 shows a first step of a method for fixing the surgical device according to the present invention to a pedicle screw;

FIG. 14 shows a second step of a method for fixing the surgical device according to the present invention to a pedicle screw;

FIG. 15 shows a third step of a method for fixing the surgical device according to the present invention to a pedicle screw.

DETAILED DESCRIPTION OF THE INVENTION

Figure 7:
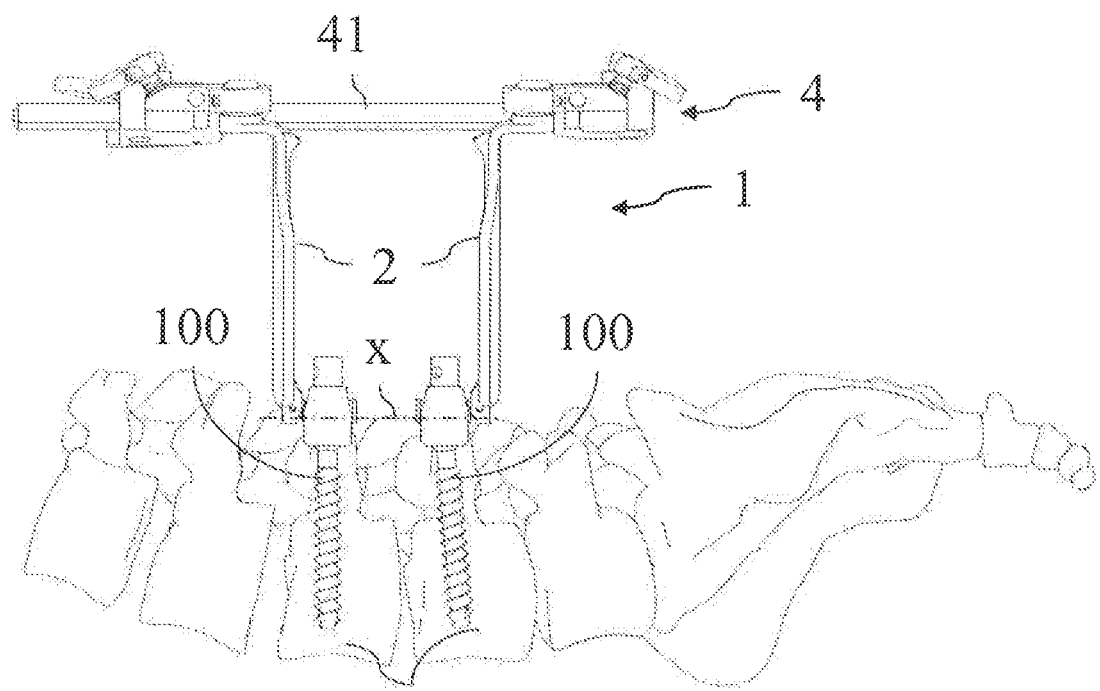
FIG. 7 shows a front view of the surgical device of FIG. 3 with its connection pins attached, in which the connection pins are locked to pedicle screws anchored to a vertebral site of a patient.
Figure 8:
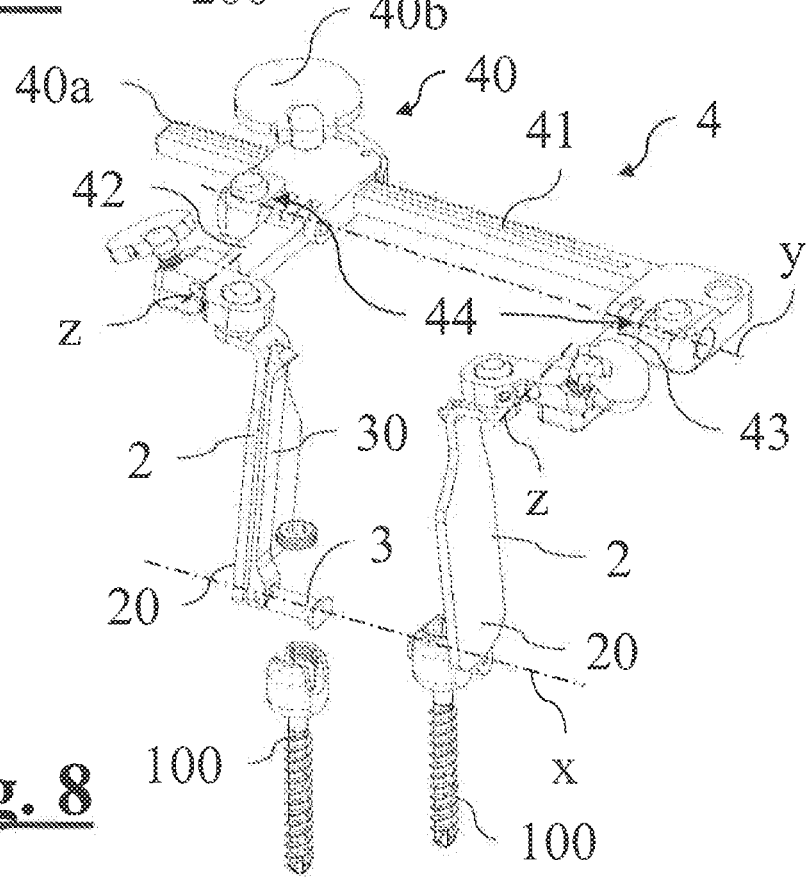
FIG. 8 shows a perspective view of the surgical device in FIG. 7 without depicting the patient's vertebral site.
Figure 9:
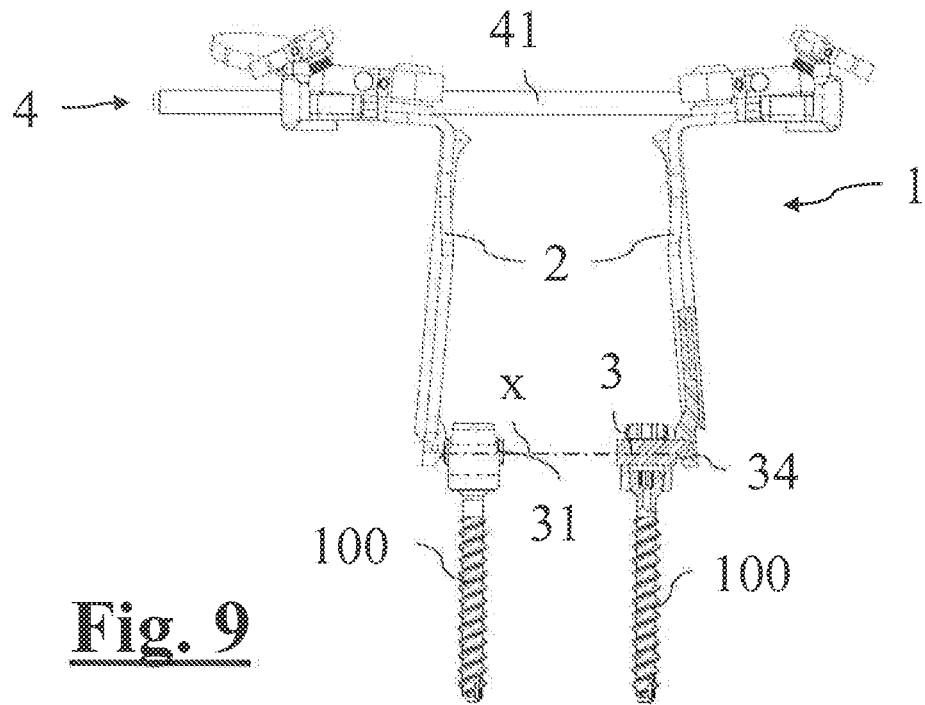
FIG. 9 shows a front view, in partial cross-section, of the surgical device in FIG. 8.

Referring to FIGS. 7-9, a surgical device 1 for minimally invasive spinal surgery is illustrated, complete with all its parts.

The surgical device 1 is mainly intended for performing posterolateral interbody fusion; however it can also be employed in connection with other surgical techniques.

The surgical device comprises a common frame 4 having a main bar 41 and two articulated arms 42, 43 departing therefrom. Two retractor blades 2 are mounted at the free ends of the articulated arms 42, 43.

In the operative configuration shown in the figures, the common frame 4 holds the retractor blades 2 in a distanced relationship wherein the two blades face each other. In the following description, the sides of the blades 2 oriented toward each other will thus be named inner side, while the opposite sides will be named external sides.

As will be apparent from the following description, the common frame 4 also enables various movements of the retractor blades 2; for instance the retractor blades 2 can be spread apart and tilted in order to perform their retracting function.

Figure 1:
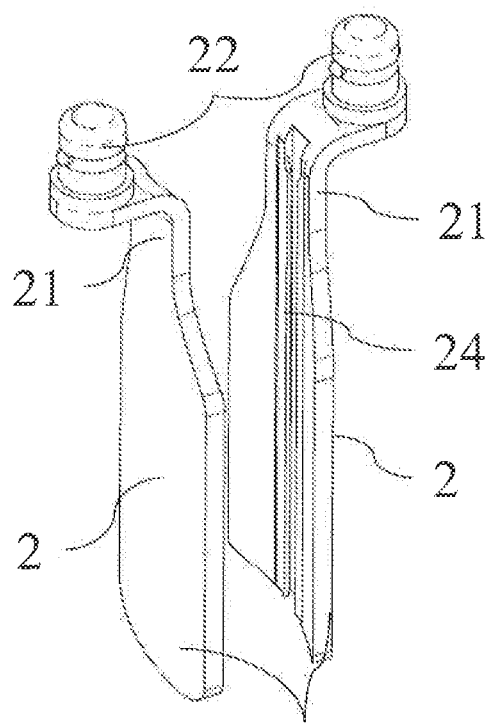
FIG. 1 shows a perspective view of the retractor blades that are part of the surgical device according to the present invention.
Figure 2:
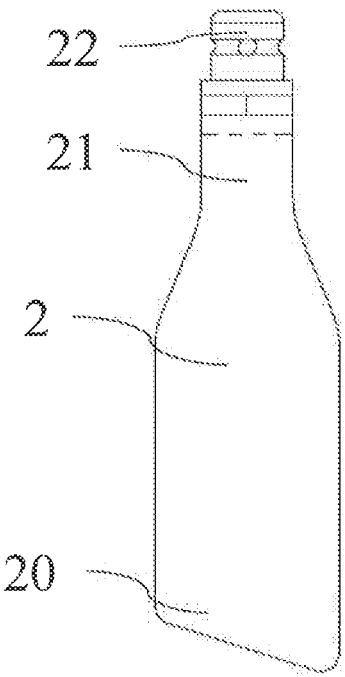
FIG. 2 shows a side view of the retractor blades in FIG. 1.
Figure 3:
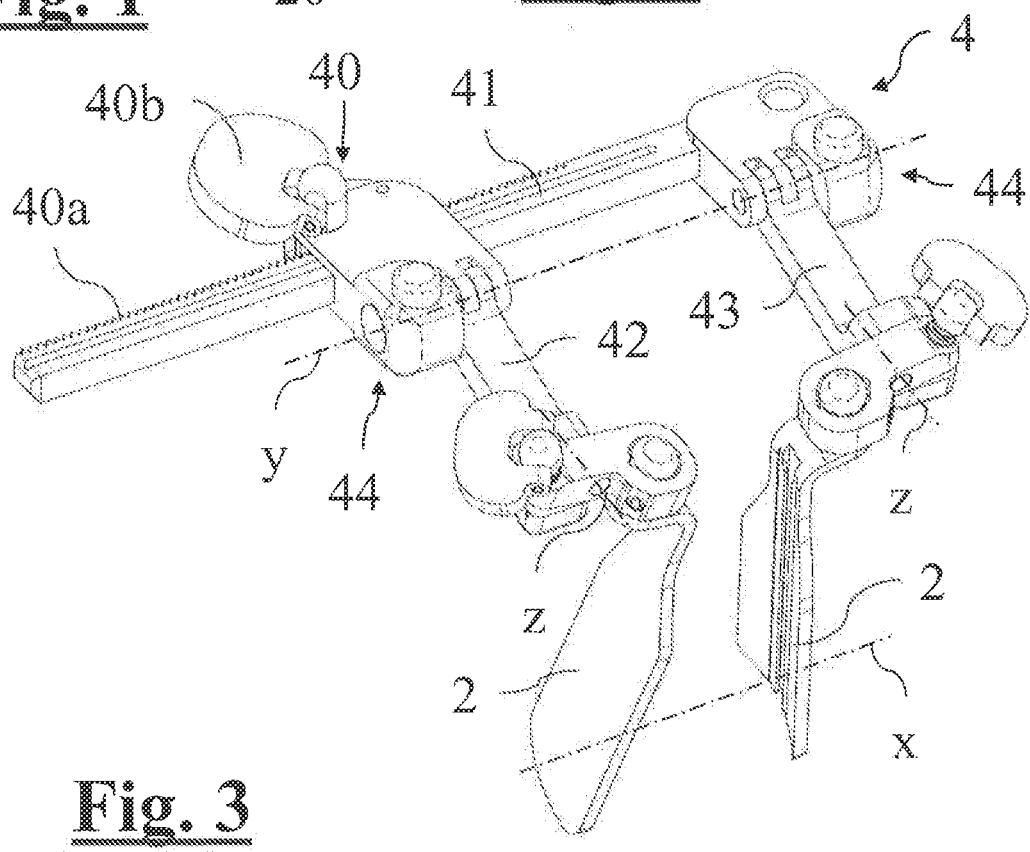
FIG. 3 shows a perspective view of a surgical device according to the present invention, with its connecting pins removed.

As best seen in FIG. 1, the retractor blades 2 are symmetrically identical, and therefore the following general description fits both of them.

A retractor blade 2 has a curved shape, featuring an convex inner side and an concave outer side, the latter being designed to press against the soft tissue of the patient during retraction.

The retractor blade extends from a proximal end 21 which is attached to the free end of the respective articulated arms 42, 43, to a distal end 20 that is intended for insertion into the surgical incision.

The distal end 20 is skewed with respect to the longitudinal extension of the retractor blade 2. In the depicted embodiment, the dimension of the blade decreases towards the common frame 4; however, an alternative embodiment may feature blades skewed in the opposite direction, wherein the common frame 4 is placed laterally. This particular shape is meant to match the geometry of the vertebral lamina of the patient.

The proximal end 21 has a reduced width, so as to cause the least possible amount of enlargement of the wound during skin retraction. The proximal end 21 features a final flange bending outwards and supporting a fixing peg 22.

The fixing peg 22 is meant to be releasably connected within a fixing hole at the free end of the articulated arm 42, 43.

The inner side of the retractor blade 2 features a T-shaped longitudinal groove 24, extending from the proximal end 21 to the distal end 20 and opening at both these ends.

Figures 10, 11, 12:
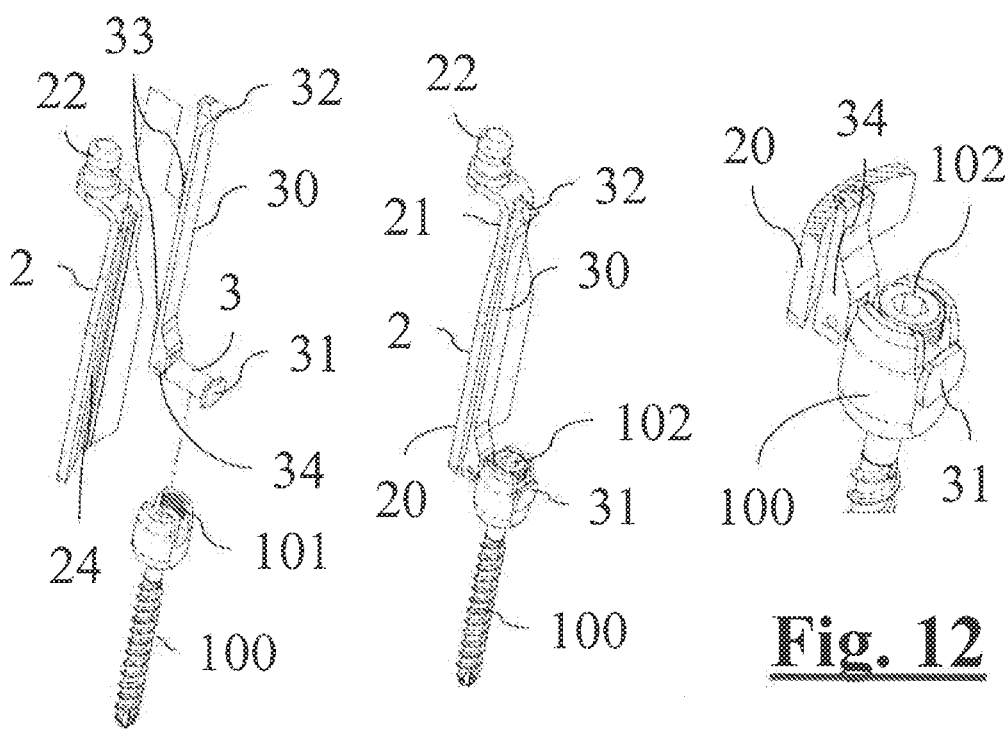
FIG. 10 shows an exploded view of a retractor blade, its connecting pin and a pedicle screw.
FIG. 11 shows a perspective view of the elements of FIG. 10 assembled together.
FIG. 12 shows a perspective view of an enlarged detail of FIG. 11.

A sliding connector 30 bearing a connecting pin 3, best seen in FIGS. 10-12, may be inserted into the longitudinal groove in order to couple the connecting pin 3 to the retractor blade 2.

The sliding connector 30 has an elongated shape and substantially the same length as the retractor blade 2. On its rear side, the sliding connector features two engaging teeth 33, spaced apart along the longitudinal axis of the connector. The engaging teeth 33 are T-shaped and are meant to be slidingly inserted within the longitudinal groove 24 of the retractor blade 2, creating the connection between the connector 30 and the blade 2.

At the proximal end, the sliding connector 30 features a thickened tail 32 meant for easy manipulation of the element. At the opposite distal end, the sliding connector 30 has a transversal hinge 34 that connects the connecting pin 3. The connecting pin 3 is therefore allowed to rotate with respect to the sliding connector, in particular a rotation of ±50° with respect to an orthogonal direction is allowed.

It is noted that the elongated sliding connector 30 may be introduced in and extracted from the proximal end of the retractor blade 2 even during surgery, i.e. when the surgical device 1 is inserted into a patient's body.

However, other types of connection between the retractor blade 2 and the connecting pin 3 may be employed, for instance a simple slotted connection.

The connecting pin 3 is a short pin ending in a retaining flange 31, having an eccentric profile for reasons that will be apparent from the following description.

The connecting pin 3 is meant to connect the retractor blade 2 to a standard pedicle screw 100 anchored to a patient vertebra. Standard pedicle screws 100 have a U-shaped passage 101 on their head for the insertion of a connecting rod. When the connecting rod is not yet in place, the connecting pin 3 may be introduced into the U-shaped passage 101 and locked therein by means of a setscrew or a dummy setscrew 102. The retaining flange 31 is located outside of the U-shaped passage 101, so that it abuts on one side of the head, retaining the pedicle screw 100 in case it is subjected to pulling forces.

When the two connecting pins 3 are respectively attached to two pedicle screws anchored to adjacent vertebrae of a patient, a diverging motion of the retractor blades 2 exerts a distraction on the vertebral bodies, so that the surgical device 1 acts as a distractor.

It is observed, therefore, that in use the connecting pins are set on a main axis x that is cranial-caudal with respect to patient anatomy.

As previously anticipated, the common frame enables relative motions of the retractor blades 2.

A first allowed motion is a relative displacement of the two retractor blades 2 along the main axis x, so as to spread apart the soft tissue of the patient and to pull the pedicle screws 100 away from each other when attached to the connecting pins 3.

The motion along the main axis x is due to the fact that one of the articulated arms 43 is fixed to the main rod 41 (conveniently parallel to the main axis x), while the other articulated arm 42 is moveable, by means of a linear actuator 40, along the same rod 41.

The linear actuator 40 is a manually operated ratchet. In fact the main rod 41 has a linear rack 40a that engages with a pinion (not visible in the figures) connected to a first portion 42a of the moveable arm 42. The pinion is solidly attached to a rotation tab 40b that may be operated by the surgeon. A pawl 40c, preventing backward motion of the moveable arm, may be released by finger pressure.

Apart from the feature of the linear actuator 40, the articulated arms 42, 43 are symmetrically identical, and therefore the following general description of the moveable arm 42 also applies, mutatis mutandis, to the fixed arm 43.

The arm comprises a first portion 42a (respectively 43a), a second portion 42b (43b) and a third portion 42c (43c).

The first portion 42a, extending from the main rod 41, is hinged to the second portion 42b about a first hinging axis y, parallel to the main axis x. An angular ratchet 44, the mechanism of which is covered by an external casing solid with the first portion 42a, blocks the angular movement of the second portion away from the distal end of the retracting blades 2, i.e. it prevents a displacement of the blades away from the surgical site. A push button 44a is provided for disengaging the pawl of the ratcheting mechanism to allow the backward rotation.

As best seen in FIG. 6, the rotation about the first hinging axis y allows a more comfortable positioning of the common frame 4 on the body of the patient.

The third portion 42c of the articulated area is a lever intermediately hinged at the free end of the second portion 42b about a second hinging axis z, parallel to the longitudinal extension of the second arm portion 42b and therefore orthogonal to the main axis x. One end of the lever lies above a protruding support 45a of the second arm portion 42b; the opposite end of the lever extends toward the opposite articulated arm and features the fixing hole meant to house the fixing peg 22 of the retractor blade 2.

The adjustment about the second hinging axis z is provided by an adjustment screw 45. A tip of the screw 45 is freely rotatable within the protruding support 45a, while the shank of the screw 45 is threadingly engaged in a through-hole of the lever end above. The adjustment screw 45 can easily be operated by the surgeon thanks to a rotation tab 45b attached to its head.

As best seen in FIG. 5, the rotation about the second hinging axis z adjusts the inclination of the corresponding blade 2.

Moreover, the orthogonal disposition of the articulated arms 42, 43 along the axis z orthogonal to the main axis x allows to have a large central passage for other instrumentation, for instance a soft tissue retractor device.

In fact according the present invention the main rod 41 is not aligned to the blade 2 but it remains always in a backward position with respect to the retractor blades (2).

On the contrary US2006/0247645 discloses a simple screw to screw distractor without any soft tissue retractor feature. Therefore the US2006/0247645 device can work for open surgeries only and not also in Mini-Open/MIS surgery due the lack of enough space for other instruments.

As previously said, the surgical device 1 is intended to be used in minimally open surgical procedures in combination with the insertion of a posterior fixation system of the spine, i.e. pedicle screws 100 with a connecting rod.

The retractor blades 2 can be placed directly after the skin incision is made and dilated, by sliding them over the dilator tube employed in the previous surgical step.

Alternatively, the pedicle screws 2 can be placed prior the application of retractor blades 2 and common frame 4, by percutaneous instruments or dilation tubes.

In this case, as best seen in FIGS. 13-15, the pedicle screw 100 is coupled to a percutaneous tower 150. The retractor blade 2, together with its connecting pin 3, may be slid over the percutaneous tower 150 according to the following steps.

It is noted that the percutaneous tower 150 features a longitudinal side opening 151 meant to allow the subsequent positioning of the connecting rod. The side opening connects with the U-shaped passage 101 of the pedicle screw 100.

In a first step depicted in FIG. 13, the retractor blade 2 is angled at 90° with respect to the percutaneous tower, so that the eccentric profile of the retaining flange 31 may enter the side opening 151.

In a second step depicted in FIG. 14, the retractor blade 2 is aligned with the percutaneous tower 150 and slid over it until the connecting pin 3 reaches the U-shaped passage 101.

In a third step, the connecting pin 3 is locked into the U-shaped passage 101 by means of a setscrew or a dummy setscrew 102 delivered through the percutaneous tower 150.

Finally, the percutaneous tower 150 is removed, the retractor blades 2 are fixed to the common frame 4, and the distraction of the vertebrae is performed by means of the linear actuator 40.

Alternatively, the distraction may be applied while the percutaneous tubes are still fixed to the pedicle screws.

Obviously a person skilled in the art, in order to meet specific needs, will readily acknowledge the possibility of changes and variations to the surgical device described above, comprised within the scope of protection as defined by the following claims.

The invention claimed is:

1. Surgical device comprising: two retractor blades facing each other and held together by a common frame, said retractor blades being insertable into a surgical incision in a patient and moveable away from each other along a main axis (x) so as to widen said surgical incision; said surgical device comprising a connecting pin attached at a distal end of each retractor blade, each connecting pin being attachable to a pedicle screw anchored to a respective vertebra of the patient, so that moving away the two retractor blades along said main axis determines a distraction of said vertebrae; said surgical device comprising a linear actuator for relatively moving the retractor blades away from each other along said main axis (x); said common frame comprising a main bar parallel to said main axis (x) and two arms coupled to said main bar and respectively holding the two retractor blades, said linear actuator moving at least one of said arms along said main bar, wherein said arms are articulated arms having first ends hinged to said main bar about hinging axis (y) parallel to the main axis (x) and second ends hinged to said retractor blades about hinging axis (z) orthogonal to the main axis (x).

2. Surgical device according to claim 1, wherein the connecting pin attached to each retractor blade is directed toward the opposite retractor blade.

3. Surgical device according to claim 2, wherein the connecting pins are orientable so as to be aligned along the main axis (x) when attached to the pedicle screws for distraction.

4. Surgical device according to claim 3, wherein each connecting pin is hingedly connected to the respective retractor blade.

5. Surgical device according to claim 2, wherein each connecting pin features a retaining flange at its free end.

6. Surgical device according to claim 2, wherein each connecting pin is releasably attached to the respective retractor blade.

7. Surgical device according to claim 6, wherein each connecting pin is mounted on a sliding connector which is slidingly attachable to an inner side of the respective retractor blade.

8. Surgical device according to claim 7, wherein said sliding connector has an elongated shape and is insertable within a longitudinal groove extending from a proximal end to the distal end of the respective retractor blade.

9. Surgical device according to claim 1, wherein an adjustment about said first hinging axis (y) is provided by an angular ratchet.

10. Surgical device according to claim 1, wherein the distal end of each retractor blade is skewed with respect to the longitudinal extension of the retractor blade.

11. Surgical system comprising a surgical device according to claim 1 and a percutaneous tower, said connecting pins being slidably engageable in longitudinal side openings of said percutaneous tower.

* * * * *